US006565539B1

(12) United States Patent
Zinger et al.

(10) Patent No.: US 6,565,539 B1
(45) Date of Patent: May 20, 2003

(54) DEVICE FOR APPLYING A FLOWABLE MEDIUM, NOTABLY A TISSUE ADHESIVE

(75) Inventors: Freddy Zinger, Raanana (IL); Igor Denenburg, Rehovot (IL); Benny Kutal, Kfar Sava (IL)

(73) Assignee: OMRIX Biopharmaceuticals SA (BE)

( * ) Notice: Subject to any disclaimer, the term of this patent is extended or adjusted under 35 U.S.C. 154(b) by 0 days.

(21) Appl. No.: 09/936,201

(22) PCT Filed: Mar. 8, 2000

(86) PCT No.: PCT/EP00/02017
§ 371 (c)(1),
(2), (4) Date: Feb. 12, 2002

(87) PCT Pub. No.: WO00/53339
PCT Pub. Date: Sep. 14, 2000

(30) Foreign Application Priority Data

Mar. 9, 1999  (DE) .......................................... 199 10 972

(51) Int. Cl.⁷ ................................................. A61M 5/00
(52) U.S. Cl. ....................................... 604/191; 604/209
(58) Field of Search .......................... 604/82, 191, 225, 604/272, 218, 35, 83–85, 236, 238, 249, 208, 131, 266, 209, 210, 211; 222/136, 137, 145.6

(56) References Cited

U.S. PATENT DOCUMENTS

| 3,606,100 A | 9/1971 | Stapf |
| 4,865,229 A | 9/1989 | Schneider et al. |
| 4,874,368 A | 10/1989 | Miller et al. |
| 4,978,336 A | 12/1990 | Capozzi et al. |
| 5,046,642 A | 9/1991 | Cathcart et al. |
| 5,520,658 A | * 5/1996 | Holm ........................ 604/191 |
| 5,582,596 A | 12/1996 | Fukunaga et al. |
| 5,584,815 A | * 12/1996 | Pawelka et al. ............ 604/191 |
| 6,394,982 B1 | * 5/2002 | Ehrenfels .................... 604/191 |

FOREIGN PATENT DOCUMENTS

| DE | 42 23 356 A1 | 7/1992 |
| DE | 19815550 | * 6/1997 |
| EP | 0 037 393 B1 | 4/1981 |
| EP | 0 315 222 B1 | 12/1984 |
| EP | 0 210 160 B2 | 6/1986 |
| EP | 0 548 509 A1 | 10/1992 |
| EP | 0919290 | * 6/1999 |
| FR | 2049299 | * 3/1971 |
| WO | WO 95/31137 | 5/1995 |
| WO | WO 96/19940 | 12/1995 |
| WO | WO 98/10703 | 9/1996 |
| WO | WO 98/40167 | 3/1997 |

* cited by examiner

Primary Examiner—Sharon Kennedy
(74) Attorney, Agent, or Firm—Diller, Ramik & Wight

(57) ABSTRACT

The device for applying a flowable medium, in particular a tissue adhesive is provided with at least one reservoir (16) for the medium, wherein said reservoir (16) comprises an outlet (22) from which the medium exits when pressure is applied to the medium and/or said reservoir (16). A pressure-generating element (20) acts upon the medium and/or said reservoir (16) and is biased by a biasing means (34). Said biasing means (34) can be locked with the aid of a controllable locking means (58), wherein said locking means (58) comprises a movable fixing element (54) which, in at least one fixing position, locks the biasing element (34) against movements caused by the biasing process, and is movable out of the at least one fixing position to release said biasing element (34). Further, a release means (81) for selected release of said locking means (58) is provided, wherein said release means (81) comprises a release element (82) for temporary movement of the fixing element (56) out of its at least one fixing position.

27 Claims, 12 Drawing Sheets

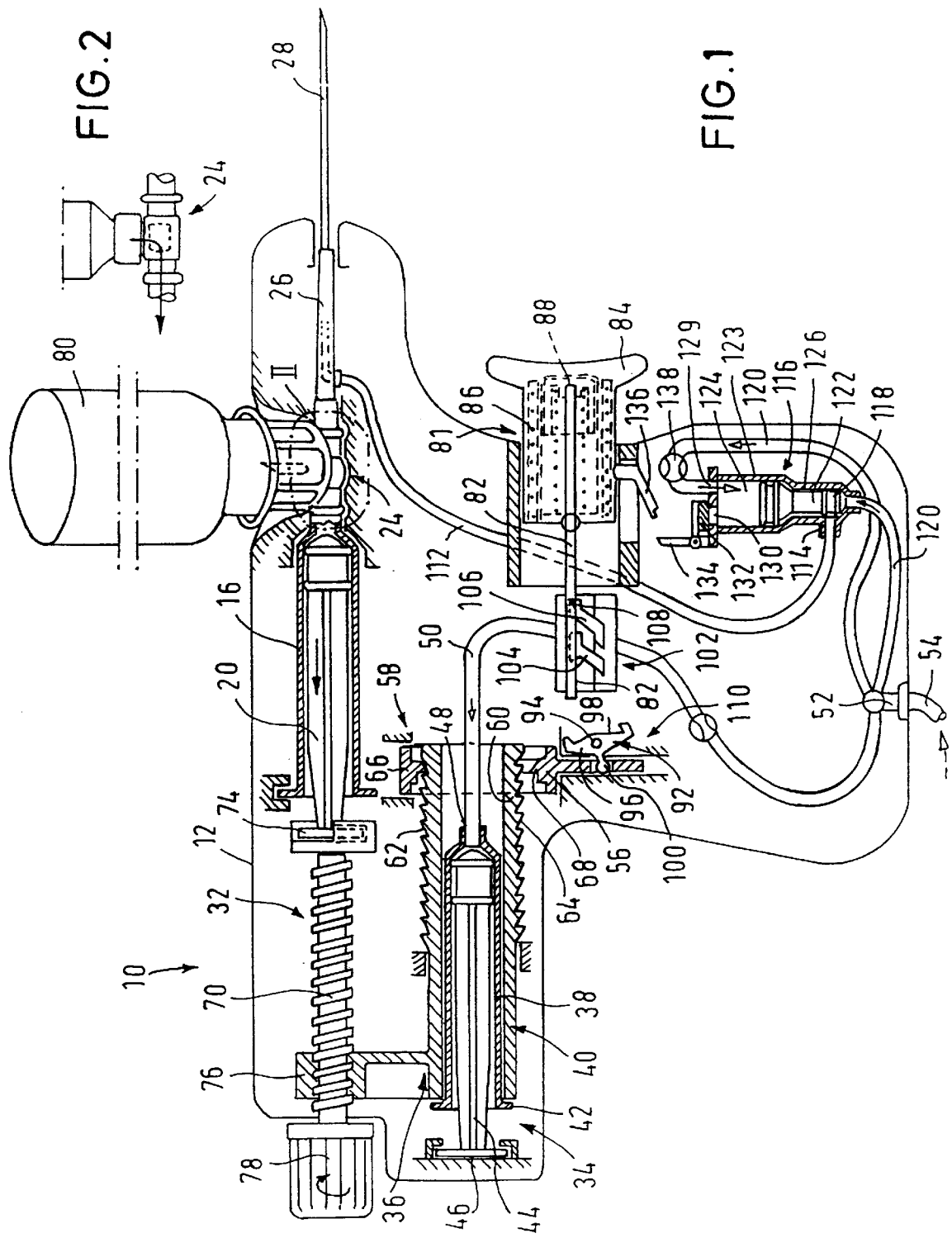

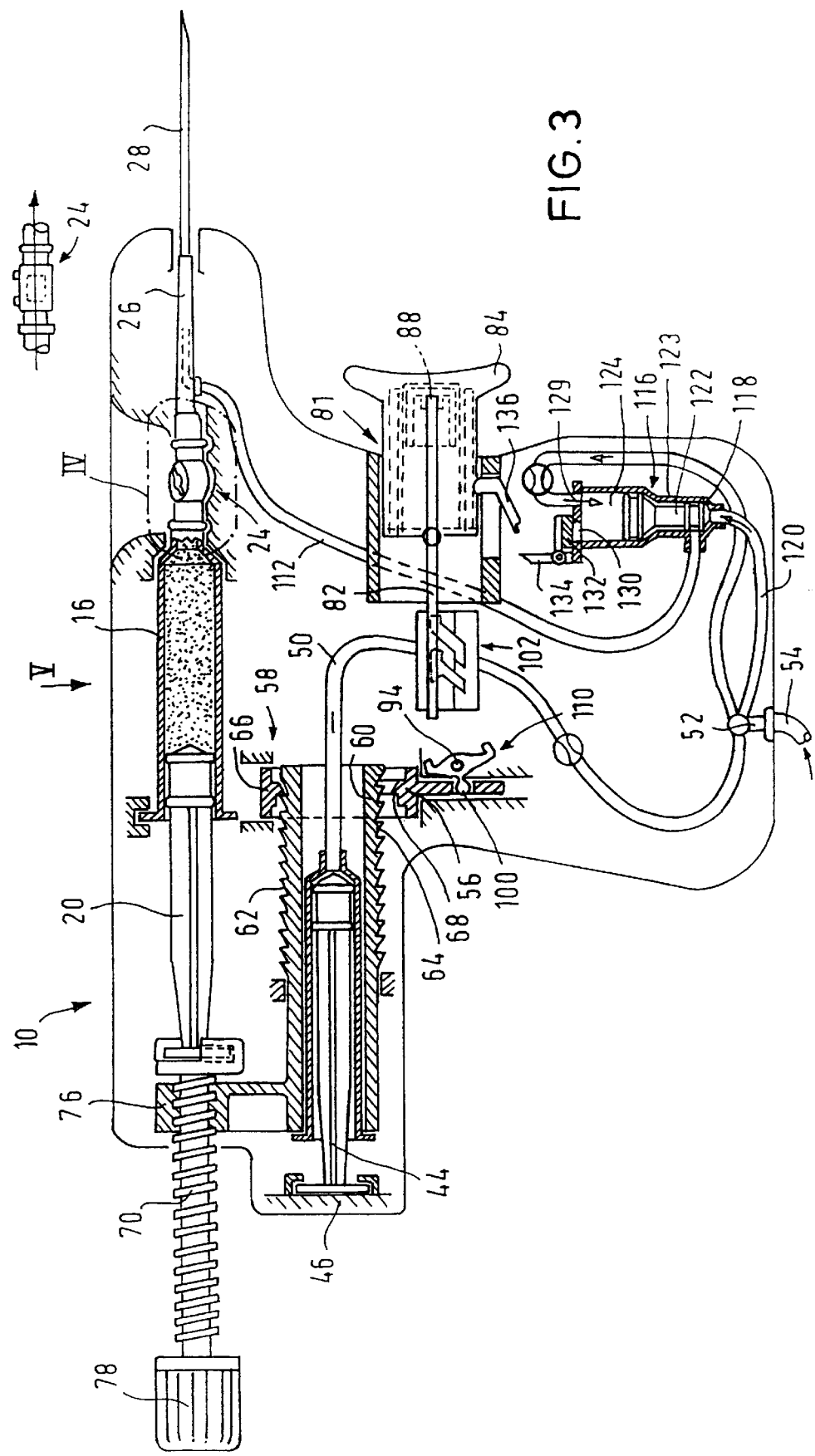

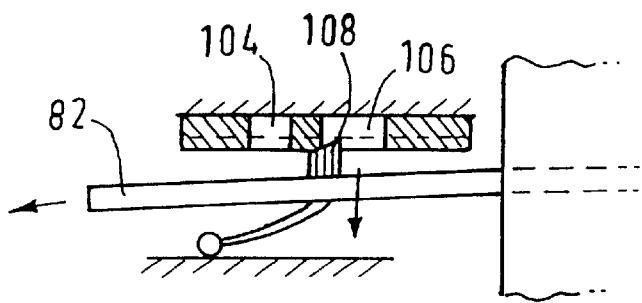
FIG. 15
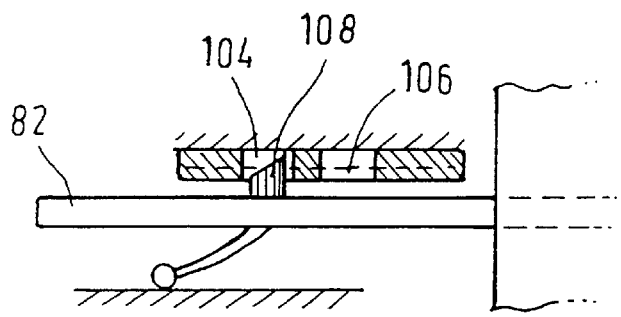
FIG. 16
FIG. 17
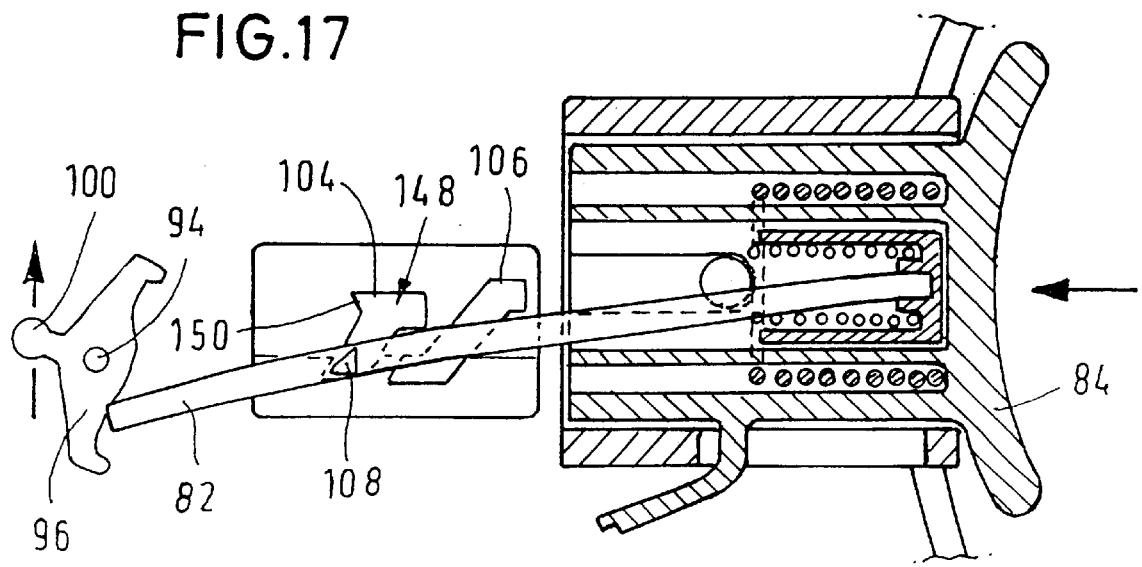

DEVICE FOR APPLYING A FLOWABLE MEDIUM, NOTABLY A TISSUE ADHESIVE

BACKGROUND OF THE INVENTION

The invention relates to a device for applying a flowable medium, in particular a single- or multiple-component tissue adhesive.

A number of embodiments of application devices for flowable media (pasty or liquid media) are known (EP-B 0 037 393, EP-B-0 210 160, U.S. Pat. No. 4,874,368, U.S. Pat. No. 4,978,336, DE-A-42 23 356, EP-B-0 315 222, WO-A-96/19940, WO-A95/31137 and WO-A-98/40167). According to the application it is sometimes necessary and desirable to dosedly discharge the medium. In the case of application devices for medical tissue adhesives it is particularly desirable that the doses are reproducible and relatively small. This discharged quantity should further be independent of the duration of manual operation of the application device.

For hygienic reasons it is further advantageous when the application devices are designed as non-returnable and/or disposable articles. This, in turn, requires the mechanisms for medium discharge in a dosed manner and independent of the application device to be of relatively simple configuration. If, besides the medium, a gas is to be discharged, by means of which the discharged medium can be sprayed onto an article, it is appropriate to control the dosing mechanism for the medium with the aid of the pressurized gas. Such an application device for technical media is known from EP-A-0 548 509. However, said known application device is not suited for use with nonreturnable and/or disposable articles due to its rather complex structure.

SUMMARY OF THE INVENTION

It is an object of the invention to provide an application device for flowable media, the application device displaying a simple structure suitable for configuration of the application device as non-returnable and/or disposable article.

According to the invention, the object is solved with an application device provided with
- at least one reservoir for the medium, the reservoir comprising an outlet from which the medium exits when pressure is applied to the medium and/or the reservoir,
- a pressure-generating element for applying pressure to the medium and/or the reservoir,
- a biasing means for biasing the pressure-generating element, the biasing means comprising a movable biasing element which is pneumatically and/or hydraulically biased towards the pressure-generating element and coupled with the latter,
- a controllable locking means for locking the biasing element, the locking means comprising a movable fixing element which, in at least in one fixing position, locks the biasing element against movements caused by the biasing process and is movable out of the at least one fixing position to release said biasing element, and
- a release means for selectedly releasing the locking means, the release means comprising a release element for temporarily moving the fixing element of its at least one fixing position.

Further aspects of the invention are stated in the subclaims.

The flowable medium to be discharged by the device according to the invention is located in a reservoir which comprises an outlet. If the medium is a multiple-component medium, the components of which are to mixed with each other only during the discharge process, a separate reservoir is provided for each component. The medium is hydraulically discharged from the reservoir by pressure application. The pressure acting upon the medium is applied by a pressure-generating element. Said pressure-generating element acts either upon the medium in the reservoir or from outside upon the reservoir which, in this case, must be of flexible configuration. In the first case, in particular a syringe is used as a reservoir, with the piston of the syringe and the piston rod serving as the pressure-generating element.

In the device according to the invention the pressure-generating element used for discharging the medium is biased. This is realized by biasing the pressure-generating element towards the reservoir with the aid of a biasing means. Said biasing means operates pneumatically and/or hydraulically, with in particular the pressure of a gas, which may be used for atomizing the discharged medium, being applied. The biasing means comprises a biasing element coupled with the pressure-generating element. Said biasing element is biased towards the pressure-generating element. The freedom of movement of the biasing element is limited by a locking means. In its normal position said locking means blocks the movement of the biasing element towards the pressure-generating means. With the aid of a release means locking of the biasing element can be released selectively and for a predeterminable period of time. Said release means comprises a release element which temporarily sets a fixing element, which locks the biasing element, into a position in which said fixing element releases the biasing element.

The biasing means appropriately comprises a medical syringe to the outlet nozzle of which a hose coupled with a compressed-gas source is connected. The piston rod end and the flanges and/or wings of the barrel of the syringe are supported between a fixed point and the biasing element. By application of pressure the piston and the piston rod are pushed out of the barrel and/or biased towards the outside. This pressure is utilized to move the biasing element towards the pressure-application element acting upon the medium reservoir.

The locking device is appropriately configured in the form of teeth meshing with each other. For this purpose the biasing means and in particular the biasing element is provided with at least one toothed rack cooperating with a fixing projection of the fixing element. If said fixing projection is in engagement with said toothed rack, movement of the biasing element is blocked. By moving the fixing element such that the fixing device is disengaged from the toothed rack the biasing means and/or the biasing element is released so that it moves in forward direction following the biasing force. Release of the biasing means and/or the biasing element is controlled by the release element which, on its part, moves the fixing element.

The toothing, i.e. the succession of teeth of the toothed rack, determines the measure by which the biasing element can move forward when it is released. If it is requested that extremely small fluid quantities are discharged, the toothed rack must display a correspondingly fine toothing. However a fine toothing is of disadvantage in so far as the meshing of the fixing projection with the toothed rack requires a high degree of finishing accuracy. This finishing accuracy is realizable only in plastic injection molded parts with higher efforts being made, which plastic injection molded parts are to be preferably employed in the device according to the invention. The reason for this is that the device according to the invention is to be configured as non-returnable and/or disposable article. Therefore it is advantageous to use toothed racks with a rougher toothing. To be able to discharge small dosing quantities even with such a tooting, it is advantageous to provide two toothed racks instead of one toothed rack at the biasing means and/or the biasing element, said toothed racks being staggered, in particular by a fraction of the distance between the teeth, preferably half the tooth distance. Consequently, the fixing element comprises two fixing projections. Said fixing projections as well as the toothed racks are arranged at opposite sides and/or sides averting each other of the fixing element and/or the biasing element. By reciprocating the fixing element a respective one of the fixing projections alternately meshes with one of the toothed racks. Even in the intermediate states of movement of the fixing element the biasing element is not released such that the desired step-by-step advance movement is limited exclusively by the alternate meshing of the fixing projections with the toothed rack and the staggered toothed rack arrangement. The fixing element is in both fixing positions protected against unintentional movements in that due to the bias a clamping force is exerted via the respective toothed rack on the fixing element. This force suffices to retain the fixing element in engagement with the respective toothed rack.

If only one toothed rack is used, mechanical biasing of the fixing element appropriately ensures that said fixing element automatically moves back into the locking position (the fixing projection meshes with the toothed rack) after release of the biasing element. The release element then operates against this biasing force in that it moves the fixing element of the locking device against the biasing force.

As has already been stated above, a mechanical coupling exists between the pneumatically and/or hydraulically biased biasing element and the pressure-generating element acting upon the fluid and/or the reservoir for the purpose of discharging the medium. The biasing element can, on the one hand, be directly coupled and/or connected with the pressure-generating element. Alternatively, coupling can be realized by employing an intermediate or connecting element. Said connecting element is appropriately configured as an actuating element for manually moving the pressure-generating element. Said actuating element is supported on the biasing element and can be manually moved relatively to said biasing element and protected against unintentional displacement. The actuating element can advantageously be configured as a spindle in threaded engagement with the biasing element. One end of said spindle is connected via a rotatably supported receiving element and/or a rotatably supported connecting element with the pressure-generating element, whereas the other end comprises a handwheel or a similar handle by means of which the spindle can be rotated. This configuration allows the pressure-generating element to be manually moved alternatively to the biasing element. This offers the advantage that the device according to the invention can optionally be used for manually discharging a medium quantity which is no longer limited in terms of volume. In the case of this application the pressure-generating element is then moved away from the biasing element by operating the spindle. If the reservoir is configured as a syringe, this spindle can also be used for taking in, via the syringe outlet, medium to be discharged from the syringe. The pressure-generating element is moved towards the biasing element by operating the spindle, whereby a vacuum is produced in the barrel of the syringe due to which vacuum the medium to be discharged (later) is taken into the barrel of the syringe.

The device according to the invention is preferably accommodated in a pistol-shaped housing, which is appropriate for the purpose of application of the medium and thus for handling purposes. Such a housing comprises a handle at which appropriately a finger-operated actuating element in the form of a pushbutton, lever or the like is arranged. For reasons of space it is further advantageous when in such a housing the reservoir containing the medium is horizontally arranged. This, in turn, means that the pressure-generating element is horizontally arranged either, i.e. moves in parallel to the movement of the actuating element. Since the pressure-generating element is coupled with the biasing element, the biasing force, too, ensures that the biasing element is movable in parallel to the actuating element. This movement of the biasing element is to be effectively blocked and/or selectively released by the fixing element when said fixing element is movable transversely to the biasing element to, on the one hand, block the biasing element and, on the other hand, release the biasing element. In the final analysis, this means that the movement of the actuating element, which releases the biasing element, must be deflected essentially by 90° to move the fixing element in transverse direction. This movement deflection means is appropriately provided with a swivelling element swivelling about a swivelling axis extending transversely to the directions of movement of the release element and the fixing element. Said swivelling element is coupled with the fixing element and comprises a swivelling arm upon which acts the release element. When the release element presses against the swivelling arm, the swivelling element is swivelled about the swivelling axis. Due to the coupling of the swivelling element with the fixing element a linear movement of the fixing element goes along with this swivelling movement. Such an arrangement is suitable for moving the fixing element from a fixing position into a release position. The fixing element is appropriately moved back from the release position into the fixing position with the aid of a biasing force mechanically applied to said fixing element.

If a structure with a fixing element alternately movable between two fixing positions is selected as locking and release mechanism, the swivelling element of the movement deflection means comprises two swivelling arms arranged opposite each other, with the release element alternately acting onto these swivelling arms. Owing to that the swivelling element is alternately pivoted in different directions, which results in a movement of the fixing element from the one fixing position into the other fixing position. In this structure the swivelling element has the form of a "T" whose horizontal legs form the two swivelling arms and whose vertical leg is coupled with the fixing element, wherein the swivelling axis is located in the point of intersection of the two legs.

As has already be said above, it is sometimes desirable to atomize the medium discharged with the aid of a device according to the invention. This requires synchronous discharge of a gas, wherein the gas should continue to be discharged for a certain time interval after termination of the medium discharge to prevent medium droplets from forming at the outlet of the device. For this purpose a valve controlling the gas discharge is preferably used, the valve being controlled by the pressure of the gas the discharge of which is to be influenced by the valve. While it is desirable that the passage state of the gas discharge valve is assumed as erratically as possible, change-over of the valve from the passage state to the blocking state is to be effected in a delayed manner. This is appropriately realized by employment of a "differential" gas discharge valve whose housing comprises two interconnected chambers with different diameters and/or cross-sectional areas. In the two chambers a piston is arranged. In particular at opposite ends of the two chambers gas inlet openings are arranged to which the pressurized gas-carrying lines are connected. In the chamber with the smaller cross-section a gas outlet is located, while the chamber with the larger cross-section contains a vent hole to be opened when required. In the normal state said vent hole is closed by a closing element.

In the blocking state of the valve the vent hole is closed. Since the associated chamber (hereinafter referred to as first chamber) has a larger cross-section than the other chamber (hereinafter referred to as second chamber) and the gas pressure is identical in both chambers, a larger force acts upon the front face of the piston located in the first chamber than upon the front face of the piston located in the second chamber. Consequently, the piston is displaced towards the second chamber until it bears upon a limit stop defined by a shoulder-shaped tapered area of the housing. In this piston position the piston seals the gas outlet of the second chamber.

By opening the vent hole the pressure in the first chamber is abruptly reduced. In the second chamber the overall gas pressure still prevails. Consequently, the piston moves into the first chamber whereby the gas outlet of the second chamber is cleared. Now the gas at the gas inlet of the first chamber is fed via the gas outlet of the first chamber; the valve is in its passage position.

As soon as the vent hole is closed again, the pressure in the first chamber rises again, namely to the value of the pressure in the second chamber. Due to the larger piston front area in the first chamber the piston moves again towards the second chamber until, in its final position, it closes the gas outlet. The velocity at which this process takes place depends, on the one hand, on the ratio of the front face sizes of the piston, and, on the other hand, on the rate at which the gas flows into the first chamber. This rate can be limited and adjusted by a flow restrictor or a similar flow rate-determining element such that the valve displays the desired time switching characteristic.

BRIEF DESCRIPTION OF THE DRAWINGS

Hereunder the invention is explained in detail with reference to the drawings in which:

FIG. 1 shows a side view of the overall setup of the device,

FIG. 2 shows a detail of FIG. 1,

FIG. 3 shows the state of the device immediately prior to application of the medium, FIG. 4 shows a detail of FIG. 3, FIGS. 12 to 25 show perspective representations as well sectional representations of the actuating element and details of said actuating element cooperating with the movement coupling of the actuating and release element with the fixing element in different phases of manual operation of the actuating element.

DESCRIPTION OF THE PREFERRED EMBODIMENTS

Figure 5:
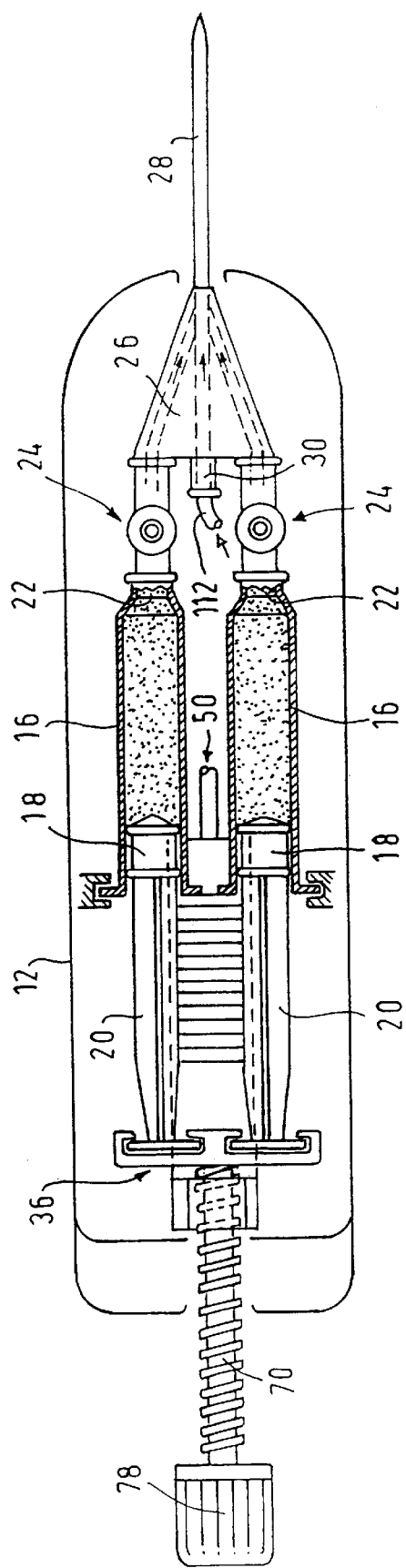
FIG. 5 shows a top view of the device according to FIG. 3.

The general setup of the device 10 according to the invention is explained in detail below with reference to FIGS. 1 to 5. The device 10 shown in the drawing serves for dosed discharge of a two-component tissue adhesive which is atomized with the aid of a gas. The device 10 comprises a housing 12 in which a double chamber discharge device 14 can be accommodated as shown in FIG. 5. Said device 14 is described in WO-A-98/10703 the contents of which is incorporated herein by reference. Said device 14 comprises two reservoirs 16 configured as syringe bodies in which pistons 18 are slidingly displaceable, said pistons 18 being arranged at piston rods 20. The outlets 22 of the syringe bodies 16 are connected via a special three-way valve 24 with the inlets of a head piece 26 at whose outlet a multiple-lumen catheter 28 is located. Further, the connecting head 26 comprises a gas connection 30. The setup of the three-way valves 24 is described in detail in WO-A-98/10703. Because of these details and the overall setup of the device 14 reference is made to the contents of this printed publication.

As can be seen from the above description, the two-component tissue adhesive is hydraulically discharged. The pistons 18 with piston rods 20 can be regarded as pressure-generating elements. A biasing means 34 acts via a connecting element 32 upon the piston rods 20, said biasing means 34 comprising a biasing element 36. Said biasing element 36 is connected via the connecting element 32 with the piston rods 20. Further, the biasing element is biased towards the piston rods 20, which, in this case, is carried out pneumatically. The flanges 42 of the syringe body 38 of a syringe 40 are supported on the biasing element 36. The piston rod 44 of said syringe 40 is supported on a locating bearing 46 of the housing 12. To the syringe outlet 48 a hose 50 is connected which is connected via a Y-type connector 52 with the connecting hose 54 coming from an external compressed-gas source. By means of the pressure building up in the syringe body 38 the piston rod 44 is pushed "in rearward direction" out of the syringe body 38 thus being pressed against the locating bearing 46. Consequently, a biasing force acts upon the biasing element 36, the biasing force pushing the the biasing element 36 "in forward direction" thus pressing it against the piston rods 20, which, in turn, exert a pressure on the medium.

By a time-limited release of the bias-induced movement of the biasing element 36 tissue adhesive can be selectedly and dosedly be discharged from the reservoirs 16. The biasing element 36 is guided in the housing 12 in an axially displaceable manner. A fixing element 56 of a locking device 58 which can engage with and disengage from the biasing element 36 controls the release and/or locking of the biasing element 36. Said fixing element 56 can be reciprocated transversely to the direction of movement of the biasing element 36. It encircles, like a ring, a sleeve-type and/or cylindrical part 60 of the biasing element 36, said part 60 being toothed at two diametrically opposed external face areas such that two rows of teeth and/or toothed racks 62,64 are produced. Opposite said rows of teeth and/or toothed racks 62,64 fixing projections 66,68 of the fixing element 56 are arranged, which alternately, according to the position of the fixing element 56, can mesh with the toothed rack 62,64 located opposite the projections and associated with them. While at the two limit points of the linear movement of the fixing element 56 the biasing element 36 is locked, the biasing element 36 is freely movable when none of the two fixing projections 66,68 meshes with the two toothed racks 62,64 during the linear movement of the fixing element 56. This particular feature is explained in detail below.

As already stated above, the biasing element 36 and the piston rods 20 are mechanically coupled with each other via the connecting element 32. Said connecting element 32 is configured as a spindle 70 which is in threaded engagement with the biasing element 36. At the end facing the piston rods 20 the spindle 70 comprises a connecting and/or receiving part 72 where the plate-type flanges 74 of the piston rods 20 are clampedly supported and which is rotatably supported on the spindle 70. The spindle 70 passes through an internally threaded extension 76 of the biasing element 36 and comprises a handwheel 78 at its end opposite the receiving part 72. By manually rotating said handwheel 78 the piston rods 20 can be displaced in the reservoirs 16 when the biasing element 36 is fixed. This function is e.g. required to take in the components of the tissue adhesive contained in ampoules 80 via the three-way valves 24 into the reservoirs 16 in the state of the device shown in FIG. 1. Further, it is possible to move the piston rods 20 into the reservoirs 16 by reverse rotation of the spindle 70 in order to manually ensure discharge of tissue adhesive.

The movement of the fixing element 56 is controlled by a release means 81 having a pin-shaped release element 82 which is reciprocable transversely to the direction of movement of said fixing element 56 when the actuating element 84 configured as an actuating button is actuated. Said actuating button 84 is arranged in the handle of the housing 12 and movable against the force of a spring 86 into said housing 12. Coaxially to the actuating button 84 a cap 88 is accommodated in said actuating button 84, said cap 88 carrying the release pin 82. Said cap 88 is also biased by a readjusting spring 90, the biasing direction of the cap 88 being identical with the biasing direction of the actuating button 84. The front end of the release pin 82 averting the cap 88 acts upon a rocker-type swivelling element 92 when the actuating button 84 is actuated, said swivelling element 92 being tiltable and/or capable of being swivelled about a swivelling axis 94 of the housing 12. Said swivelling element 92 is provided with two swivelling arms 96,98 extending linearly on both sides of the swivelling axis 94. Transversely to the swivelling arms 96,98 an extension 100 is arranged which forms one part of a ball-and-socket joint whose other part is configured on the fixing element 56. The swivelling element 92 is thus mechanically connected with the fixing element 56. By pivoting the swivelling element 92 the fixing element 56 can thus be reciprocated.

The release pin 82 is guided via a double-groove guide 102. Owing to this guiding the release pin 82 moves both linearly and excurses transversely to this direction of movement when the actuating button 84 is actuated. The double-groove guide 102 comprises two guiding grooves 104,106 extending at a slant to the linear movement direction of the release pin, with a carrier projection 108 of the release pin 82 meshing with said guiding grooves 104,106. Due to the double-groove guide 102 the release pin 82 is alternately positioned in two different advance positions, in which the release pin 82 experiences different transverse excursions, when the actuating button 84 is repeatedly pressed. For this purpose the readjusting capability of the release pin 82 transversely excursed in one or both advance positions is utilized. The double-groove guide 102 is operated in a similar way as cartridge writing utensils where the cartridge is moved into an extended position, in which it is locked, and a retracted position by repeatedly pressing an actuating button.

Employment of this known double-groove guide 102 in the device 10 offers the advantage that in the case of repeated actuation of the actuating button 84 the rocker-type swivelling element 92 is alternately tilted and/or pivoted in opposite directions such that, due to repeated actuation of the actuating button 84, the fixing element 56 is reciprocable between its fixing positions by the movement deflection means 110 realized by the swivelling element 92, in which positions it alternately meshes with one of the two toothed racks 62,64 and locks the biasing element 36.

By pressing the actuating button 84 not only the medium discharge but also the gas discharge is controlled in the device 10. To the gas connection 30 of the connecting head piece 26 a hose 112 is connected which is connected with the gas outlet connection 114 of a gas pressure-controlled valve 116. Said valve 116 comprises a gas inlet 118 to which a hose 120 is connected which is connected with the Y-type connector 52. Via the gas inlet 118 the gas to be controlled is supplied to the valve 116 and is allowed to pass to the gas outlet 114 and thus to the connecting head piece 26 in dependence on the position of a control piston 122. Said valve 116 comprises a valve housing 123 having a first or control chamber 124 and a second or gas passage chamber 126 which is provided with the gas inlet 118 and the gas outlet 114. The first chamber 124 has a larger cross-section than the second chamber 126. The control piston 122 effects sealing with its end with the larger cross-section in the first chamber 124 and with its end with the smaller cross-section in the second chamber 126. Into the first chamber 124 extends a control line 128 connected to a gas inlet 129 of said chamber 124 and connected to the Y-type connector 52. In the first chamber 124 a vent hole 130 is provided which is closed by a closing element 132 biased into a closed position. Said closing element 132 comprises an actuating arm 134 arranged in the movement path of a carrier element 136 which is connected with the actuating button 84.

In the normal position the valve 116 assumes its closed state in which the control piston 122 is inserted into the second chamber 126 to such an extent that it closes the gas outlet 114. This state is assumed due to the fact that gas with identical gas pressure acts on both sides of the piston, and a displacement force acting upon the piston 122 occurs in the direction of the second chamber 126 due to the different sizes of the piston front faces. By opening the vent hole 130 the pressure in the first chamber 124 is abruptly reduced. This results in displacement of the control piston 122 into the first chamber 124 and clearing of the gas outlet 114 such that a fluid connection between the gas inlet and the gas outlet 114 is produced. As soon as the vent hole 130 is closed again, the control piston 122 returns into its closed position. To delay this movement and prevent this movement from being carried out abruptly, the control line 128 contains a flow restricting element 138 in the form of a flow restrictor or the like.

Figure 6:
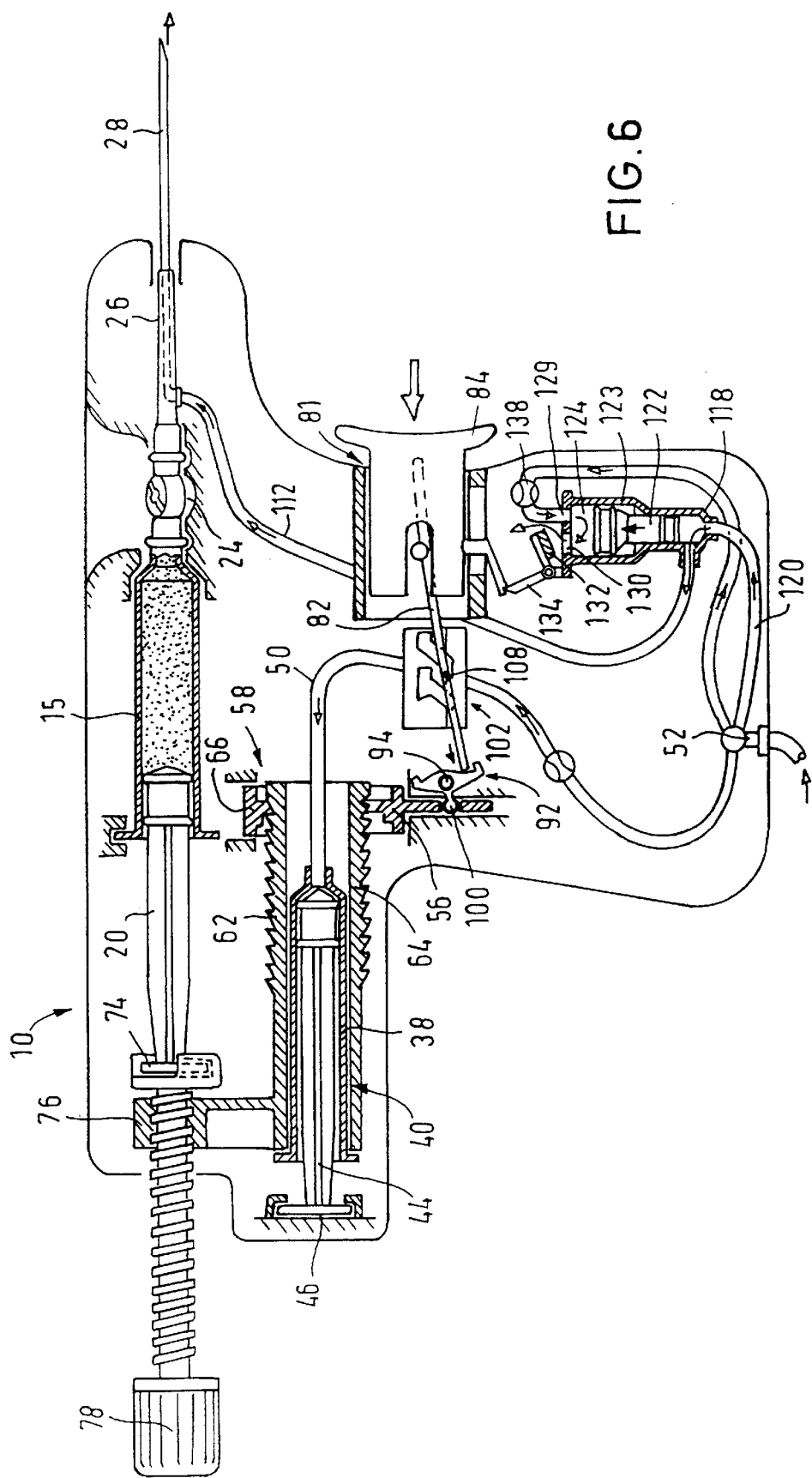
FIG. 6 shows the device in the state after initial operation of the actuating element and immediately before exit of the medium.
Figure 7:
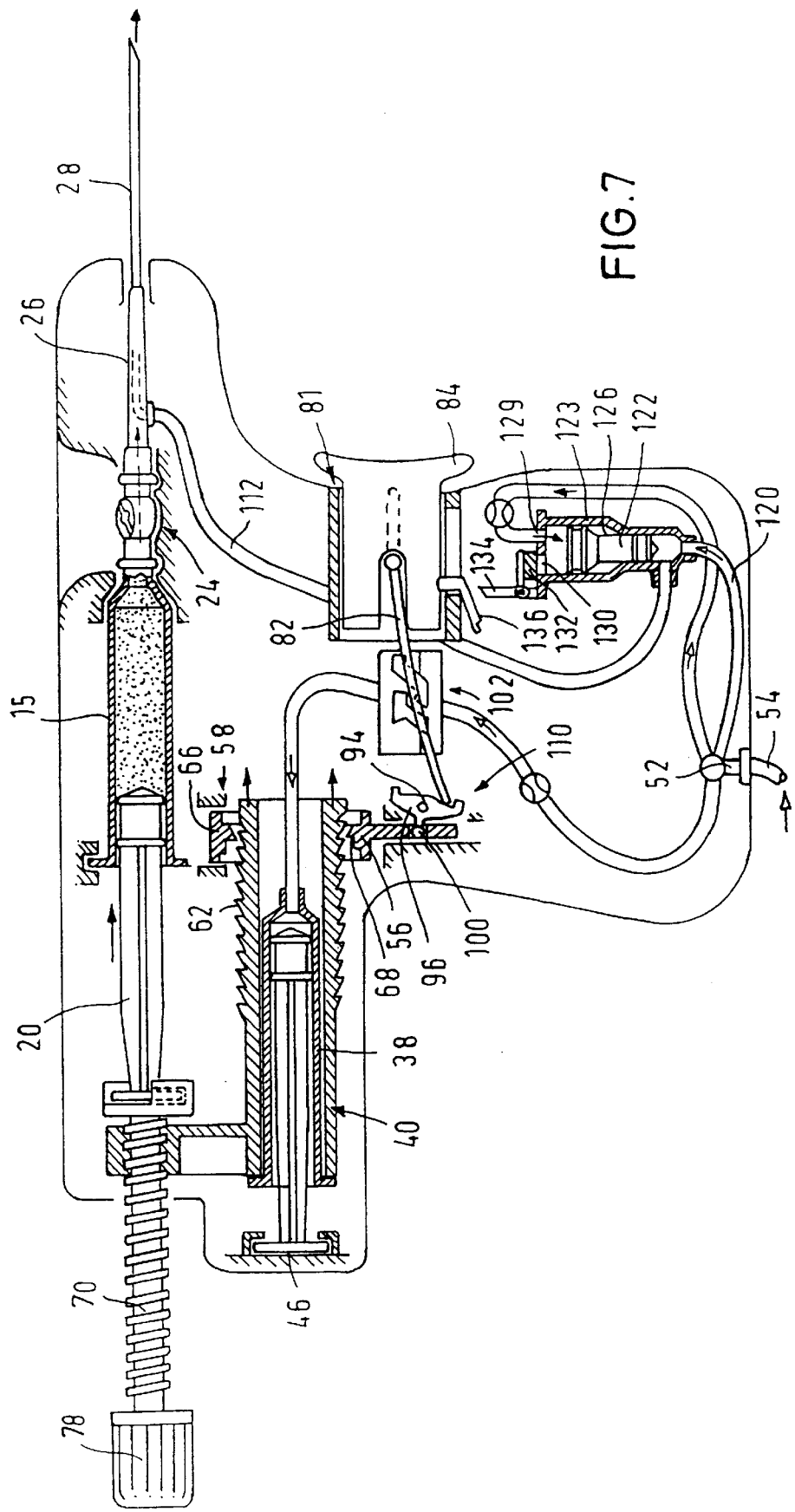
FIG. 7 shows the state of the device when the actuating element is in an intermediate position, and in the phase in which the medium exits.
Figure 8:
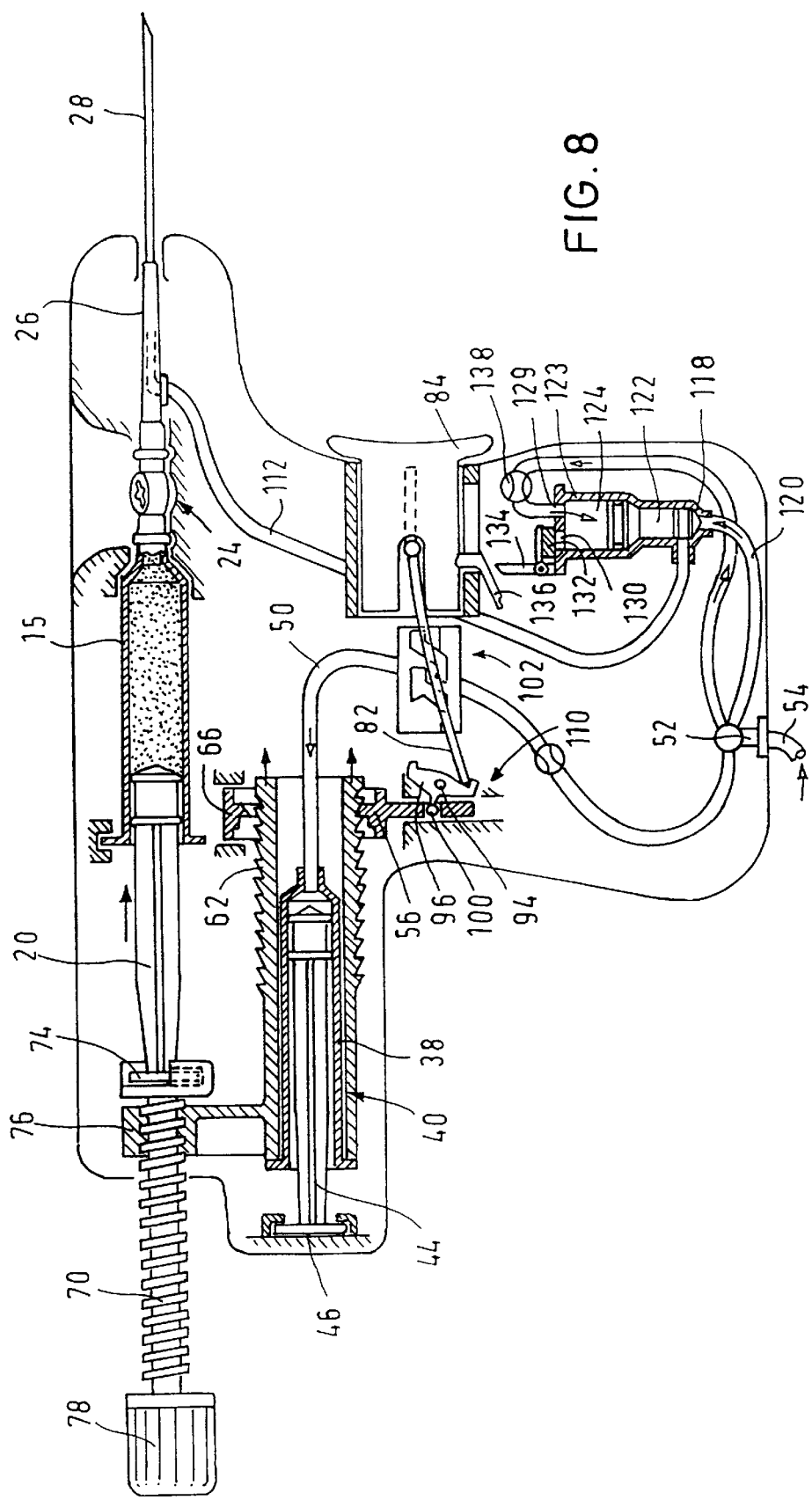
FIG. 8 shows the state of the device with fully pushed-through actuating element and stopped medium discharge.

Now that the basic setup of the device 10 has been described, it can be seen from FIGS. 6 to 9 which intermediate operating stages the device 10 assumes in dependence on the actuation of the actuating button 84. By pressing the actuating button 84 not only the tissue adhesive discharge but also the gas discharge is controlled. As can be seen in FIG. 6, the valve 116 is operated at the beginning of actuation of the actuating button 84, wherein the control piston 122 clears the gas outlet 114 as a result of pivoting the closing element (see FIG. 6). Now gas flows out of the catheter 28. At this time the release pin 82 does not yet bear upon the swivelling element 92 and/or just bears upon the swivelling element 92. Upon further actuation the release pin 82 presses onto the swivelling arm 98 of the swivelling element 92 whereby the latter is pivoted and thus the fixing element 56 is moved out of the locking position assumed before and via a temporarily assumed release position into the second locking position. For the duration during which none of the fixing projections 66,68 of the fixing element 56 meshes with the toothed racks 62,64 the biasing element 36 can move in forward direction thus moving the piston rods 20 into the reservoirs 16. Consequently, the tissue adhesive is discharged via the catheter 28 (see FIGS. 6 and 7). When the actuating button 84 is fully pushed (see FIG. 8), the closing element 132 closes the vent hole 130 of the valve 116. Thus the control piston 122 moves in a time-delayed manner back into the second chamber 126 and closes the gas outlet 114 when it has assumed its final position. This means that for a short time after the discharge of tissue adhesive gas flows out of the catheter 28. If a tissue adhesive droplet forms at the end of the catheter 28, this droplet is atomized by the gas flow.

Figure 9:
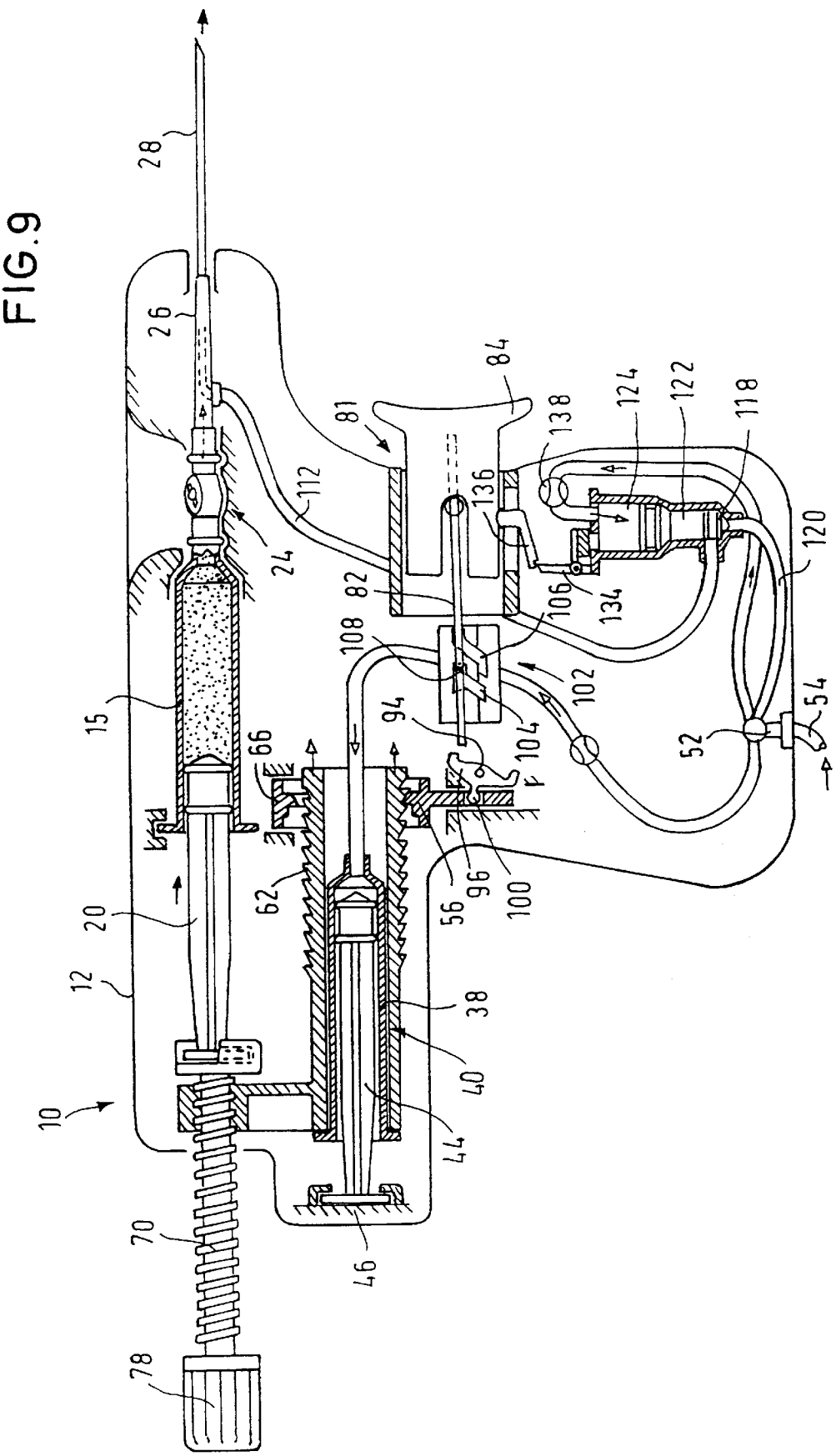
FIG. 9 shows the state of the device after complete release of the actuating element.

After release of the actuating button 84 the situation shown in FIG. 9 occurs. As can be seen, the release pin 82 is in a position further inside the housing 12 as compared with the position shown in FIG. 1, wherein its free end is located opposite the swivelling arm 96 upon which the release pin 82 has not acted during the previous advance movement. This means that during the next actuation of the actuating button 84 the release pin 82 acts upon the swivelling arm 96 which results in the fixing element 56 being moved from the position shown in FIG. 9 into the position shown in FIG. 1.

Figure 10:
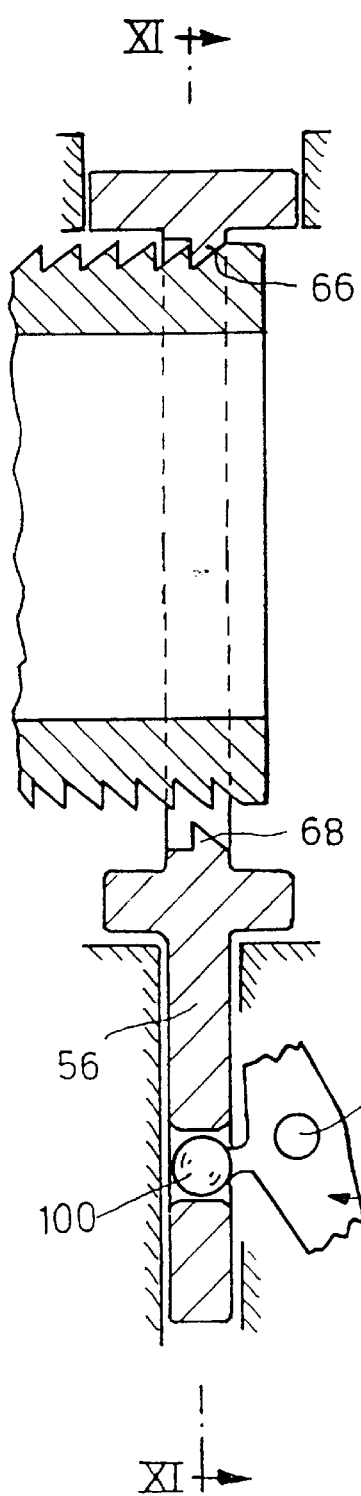
FIGS. 10 and 11 show enlarged representations of the locking and release mechanisms.
Figure 11:
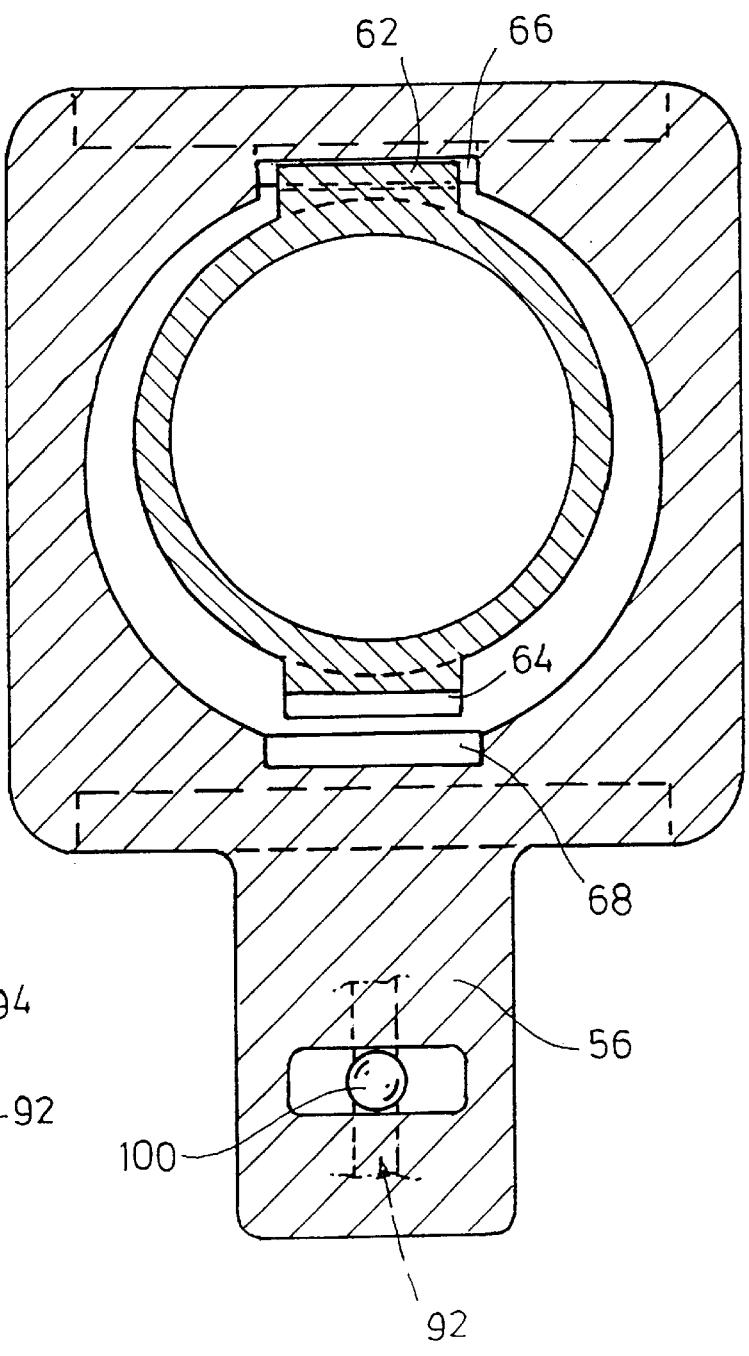
Figure 12:
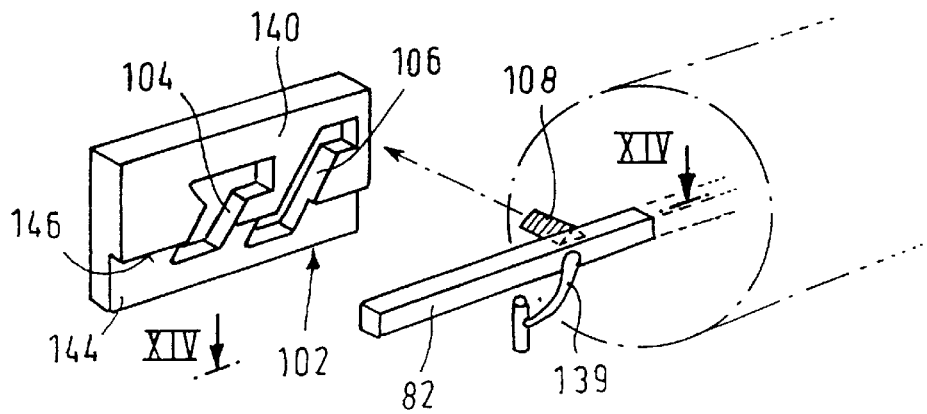
Figure 13:
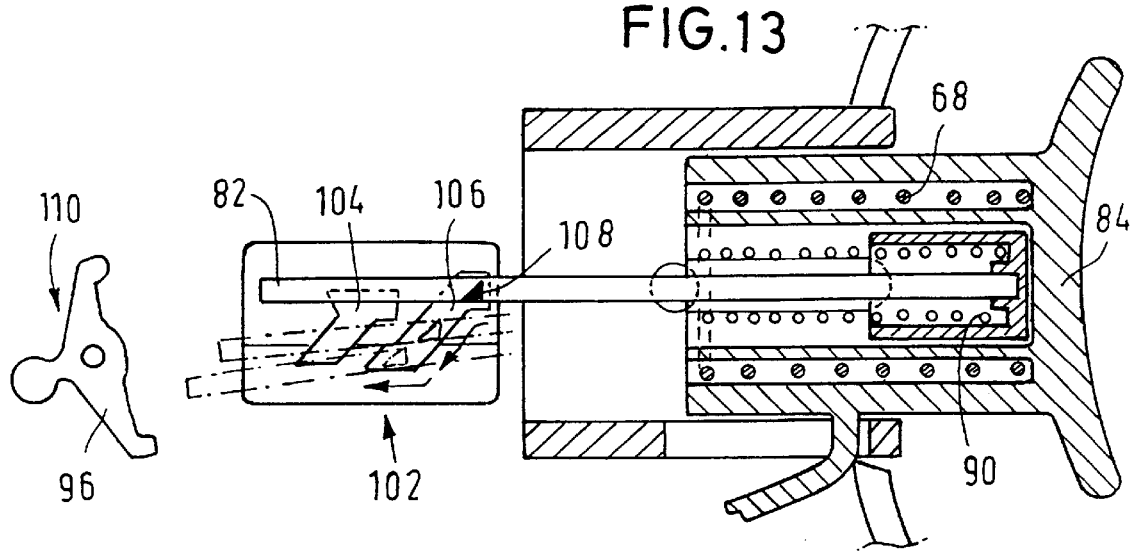
Figure 14:
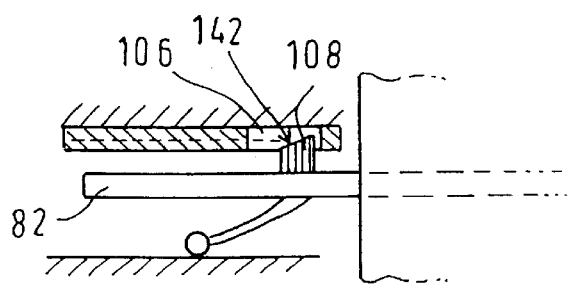
Figure 18:
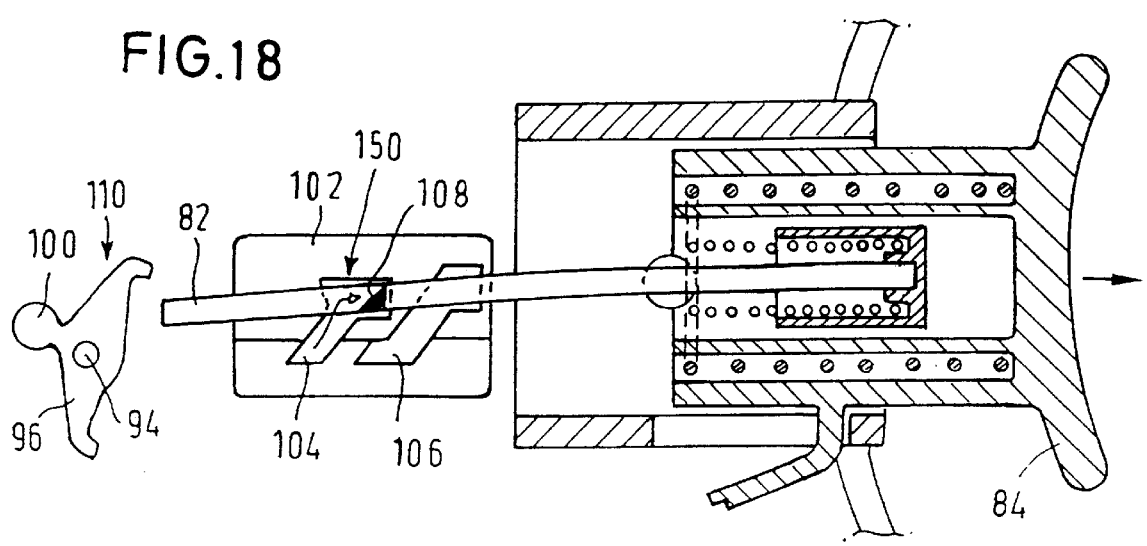
Figure 19:
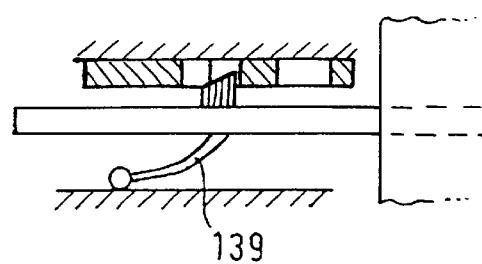
Figure 20:
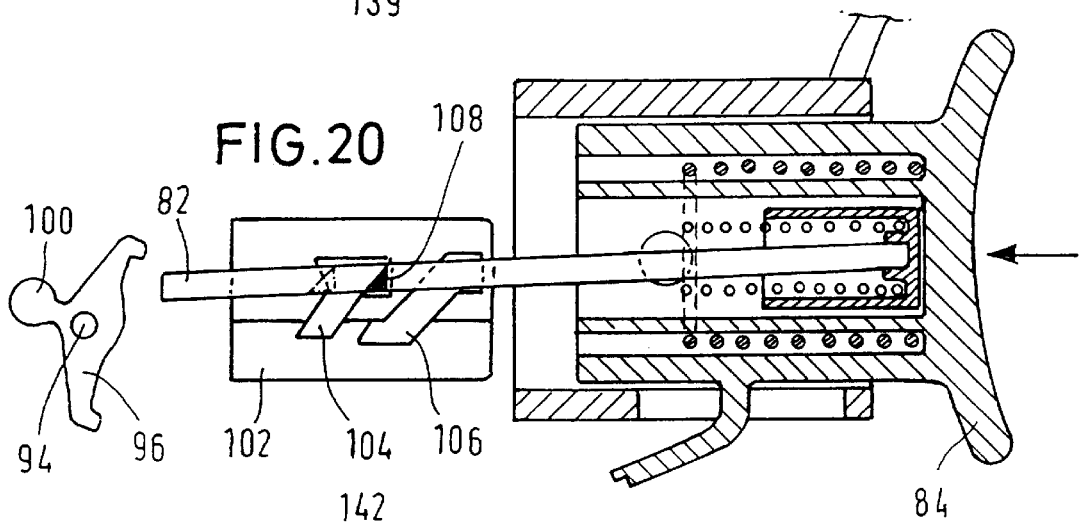
Figure 21:
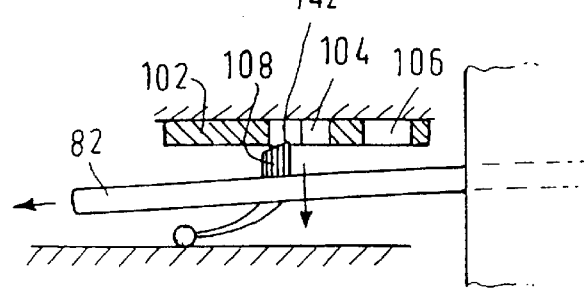
Figure 22:
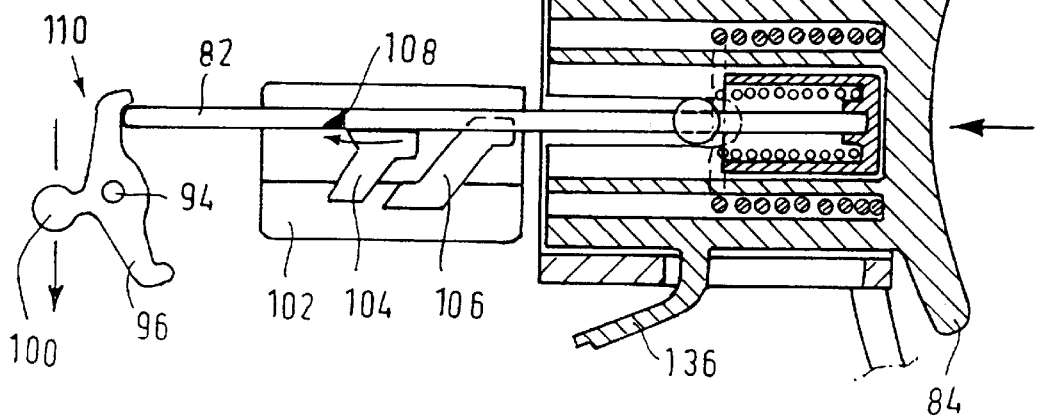
Figure 23:
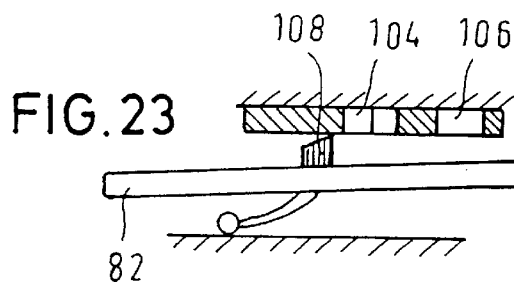
Figure 24:
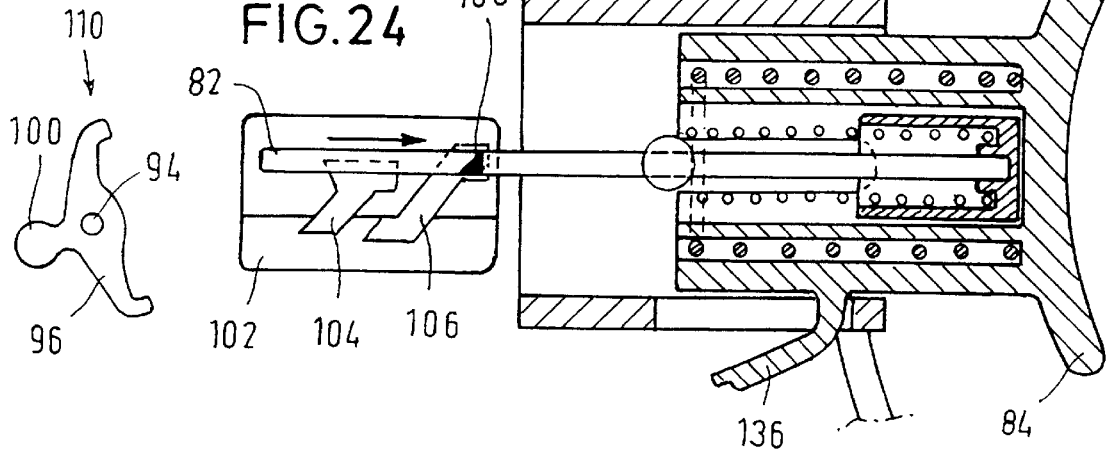
Figure 25:
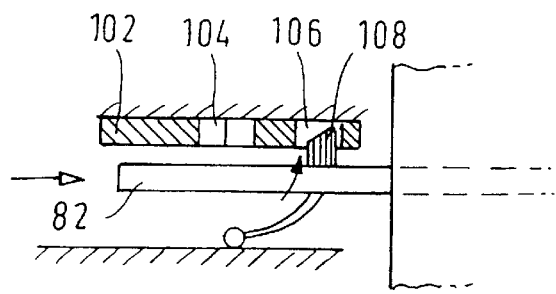

FIGS. 10 and 11 show, on an enlarged scale, the cooperation and the configuration of the fixing element 56 and the cylindrical part 60 of the biasing element 36. The fixing element 56 encircles, like a ring, the part 60 of the biasing element 36, and its fixing projections 66,68 alternately, according to the displacement position, mesh with one of the two toothed racks 62,64.

As shown in FIGS. 13, 17, 18, 20, 22 and 24, the two readjusting springs 86,90 set the elements (actuating button 84 and cap 88) coupled with said readjusting springs 86,90 into an extended position. Since, due to the double-groove guide 102 with the guiding grooves 104,106 arranged one behind the other as seen in the direction of movement of the release pin 82, the position of the release pin 82 differs, but, irrespective of this, the actuating button 84 is to be returned always into one and the same initial position after having been released, the second spring 86 is required, besides the first spring 90 acting upon the cap 88, for moving the actuating button 84 back. If this double spring arrangement did not exist, the actuating button 84, in the state shown in FIG. 18, would not be fully moved back. This is however necessary, on the one hand for reasons of an improved haptics and handling of the device 10, and on the other hand due to actuation of the closing element 132 of the valve 116 by means of the pushbutton 84.

FIGS. 12 to 25 further show that the release pin 82 is moved against the plate 140 via an integrally formed spring arm 139, the plate 140 comprising the two guiding grooves 104,106. This pressing is appropriate to ensure, irrespective of any vibrations acting upon the release pin 82, that the carrier projection 108 of the release pin 82 remains in engagement with one of the two guiding grooves 104,106.

Finally, FIGS. 12 to 25 show the advance and pivoting positions of the release pin 82 in dependence on the position of the actuating button 84 and its actuation sequence. The following description is based on the situation shown in FIG. 13. In this position the carrier projection 108 of the release pin 82 is in the first guiding groove 106 relative to the advance movement of the release pin 82 towards the swivelling element 110. When the actuating button 84 is acutated the release pin 82 is forcedly moved downwards (relative to the representation in the FIGS.)(as shown by the dot-dash line in FIG. 13). When the carrier projection 108 has reached at the end of the guiding groove 106, the release pin 82 is moved away from the plate 140, since the carrier projection 108 comprises a bevelled face 142 at its free front end, said bevelled face 142 causing this extending movement of the release pin 82 when the carrier projection 108 has reached the end of the guiding groove 106 and a force continues to act upon the actuating button 84. To prevent the release pin 82 pivoted into this position from moving back into its linear position shown in FIG. 13 due to its readjusting capability when the carrier projection 108 is moved out of the guiding groove 106, the plate 140 comprises a graduated portion 144 with a guiding edge 146 along which the carrier projection 108 slides up to the second guiding groove 104 as long as it is outside the guiding groove 106 (see the intermediate positions shown in FIGS. 15 to 17). The guiding edge 146 thus connects the ends, shown in the lower section of the drawing plane, of the two slanting guiding grooves 106,104 of the double-groove guide 102.

In the position shown in FIG. 17 the carrier projection 108 is located in the guiding groove 104 facing the swivelling element 110. Further, the guiding pin 82 acts upon the swivelling element 110 and rotates said element. When the actuating button 84 has been released, the guiding pin 82 is moved back by the readjusting spring 90 until the carrier projection 108 bears upon the end of the guiding groove 104 facing the actuating button 84 (see FIGS. 18 and 19). If, proceeding from this position, the actuating button 84 is pushed again (see FIGS. 20 and 21), the release pin 82 is moved again in forward direction towards the swivelling element 110. Meshing of the carrier projection 108 with the guiding groove 104 would result in an excursion movement of the release pin 82 transverse to the direction of its linear movement. The guiding groove 104 comprises however a trapping recess 150 in its bend area 148 (see FIG. 17) into which trapping recess 150 the carrier projection 108 is inserted (see FIG. 21). Thus the carrier projection 108 does not follow the further slanting course of the guiding groove 104 but rather moves out of the guiding groove 104 via the bevelled face 142, more precisely, out of the trapping recess 150. Thus the release pin 82 moves essentially linearly in forward direction, has however a certain readjusting capability due to a slight excursion. This readjusting capability has the effect that the release pin 82 linearly aligns itself, and its carrier projection 108 is placed into a position above the guiding groove 104 (see FIG. 22). Besides the fact that the release pin 82 acts upon the swivelling element 110 as the release pin 82 continues to move in forward direction (see FIGS. 22,23), the movement of the carrier projection 108 up to the area above the guiding groove 104 has the effect that the carrier projection 108 laterally slides past the upper end of the guiding groove 104 when the pushbutton 84 is released (see FIG. 24) in order to mesh with the upper end of the guiding groove 106 (see FIGS. 24 and 25). At this point the same movements as described with reference to FIG. 12 are started again when the pushbutton 84 is actuated the next time.

Although a preferred embodiment of the invention has been specifically illustrated and described herein, it is to be understood that minor variations may be made in the apparatus without departing from the spirit and scope of the invention, as defined the appended claims.

What is claimed is:

1. A device for applying a flowable medium, in particular a tissue adhesive, the device comprising:
   at least one reservoir (16) for the medium, the reservoir (16) comprising an outlet (22) from which the medium exits when pressure is applied to the medium and/or the reservoir (16),
   pressure-generating element (20) for applying pressure to the medium and/or the reservoir (16),
   biasing means (34) for biasing the pressure-generating element (20), said biasing means (34) comprising a movable biasing element (36) which is pneumatically and/or hydraulically biased towards said pressure-generating element (20) and coupled with the latter,
   controllable locking means (58) for locking the biasing element (36), said locking means (58) comprising a movable fixing element (56) which, in at least in one fixing position, locks said biasing element (36) against movements caused by the biasing process and is movable out of the at least one fixing position to release said biasing element (36), and
   release means (81) for selectively releasing the locking means (58), said release means (81) comprising a release element (82) for temporarily moving the fixing element (56) out of its at least one fixing position,
   wherein the biasing means (34) comprises a first and a second toothed rack (62,64) coupled with the biasing element (36), and the fixing element (56) comprises a first fixing projection (66) for meshing with the first toothed rack (62) and a second fixing projection (68) for meshing with the second toothed rack (63), and
   wherein the two toothed racks (62,64) avert each other and the two fixing projections (66,68) face each other, and the fixing element (56) is reciprocal by the release element (82) between two fixing positions in which one of the fixing projections (66,68) meshes with one of the toothed racks (62,64).

2. The device as defined in claim 1 wherein the biasing means (34) comprises a fluid pressure cylinder (38) with a piston (44) which are arranged between a fixed point (46) and the biasing element (36) and/or in said biasing element (36), and that said fluid pressure cylinder (38) comprises a connection (48) for a fluid pressure line (50) to which a fluid pressure source can be connected or with which a fluid pressure source can be coupled.

3. The device as defined in claim 1 wherein the biasing element (36) is directly connected and/or connectable with the pressure-generating element (20).

4. The device as defined in claim 2 wherein the biasing element (36) is directly connected and/or connectable with the pressure-generating element (20).

5. The device as defined in claim 1 wherein the biasing element (36) is coupled with the pressure-generating element (20) via an actuating element (32) for manually moving the pressure-generating element (20), wherein said actuating element (32) is guided along the biasing element (36), in a displaceable manner and protected against unintentional displacement, and connectable with said pressure-generating element (20).

6. The device as defined in claim 2 wherein the biasing element (36) is coupled with the pressure-generating element (20) via an actuating element (32) for manually moving the pressure-generating element (20), wherein said actuating element (32) is guided along the biasing element (36), in a displaceable manner and protected against unintentional displacement, and connectable with said pressure-generating element (20).

7. The device as defined in claim 3 wherein the biasing element (36) is coupled with the pressure-generating element (20) via an actuating element (32) for manually moving the pressure-generating element (20), wherein said actuating element (32) is guided along the biasing element (36), in a displaceable manner and protected against unintentional displacement, and connectable with said pressure-generating element (20).

8. The device as defined in claim 5 wherein the actuating element (32) comprises a spindle (70) which is in threaded engagement with the biasing element (36), which spindle (70) is at its one end rotatably connected with a connecting element (72) for the pressure-generating element (20) and comprises at its other end a handwheel (78) for manually rotating said spindle (70).

9. The device as defined in claim 1 wherein the release means (81) comprises a manually movable actuating element (84) for moving the release element (82), wherein said release element (82) moves at an angle to the direction of movement of the fixing element (56), and a movement deflection means (110) is arranged between the two elements.

10. The device as defined in claim 2 wherein the release means (81) comprises a manually movable actuating element (84) for moving the release element (82), wherein said release element (82) moves at an angle to the direction of movement of the fixing element (56), and a movement deflection means (110) is arranged between the two elements.

11. The device as defined in claim 3 wherein the release means (81) comprises a manually movable actuating element (84) for moving the release element (82), wherein said release element (82) moves at an angle to the direction of movement of the fixing element (56), and a movement deflection means (110) is arranged between the two elements.

12. The device as defined in claim 4 wherein the release means (81) comprises a manually movable actuating element (84) for moving the release element (82), wherein said release element (82) moves at an angle to the direction of movement of the fixing element (56), and a movement deflection means (110) is arranged between the two elements.

13. The device as defined in claim 5 wherein the release means (81) comprises a manually movable actuating element (84) for moving the release element (82), wherein said release element (82) moves at an angle to the direction of movement of the fixing element (56), and a movement deflection means (110) is arranged between the two elements.

14. The device as defined in claim 1 wherein the movement means of release element (82) extends at right angles to the direction of movement of the fixing element (56).

15. The device as defined in claim 9 as defined in the movement deflection means (110) comprises a swivelling element (92) swivelling about a swivelling axis (94) extending transversely to the directions of movement of the release element (82) and the fixing element (56), and being movably coupled with the fixing element (56), and comprising at least one swivelling arm (96,98) upon which acts the release element (82) for rotating said swivelling element (92) and thus displacing said fixing element (56) when the actuating element (84) is actuated.

16. The device as defined in claim 14 as defined in the movement deflection means (110) comprises a swivelling element (92) swivelling about a swivelling axis (94) extending transversely to the directions of movement of the release element (82) and the fixing element (56), and being movably coupled with the fixing element (56), and comprising at least one swivelling arm (96,98) upon which acts the release element (82) for rotating said swivelling element (92) and thus displacing said fixing element (56) when the actuating element (84) is actuated.

17. The device as defined in claim 15 wherein the swivelling element (92) comprises two opposite swivelling arms (96,98) upon which alternately acts the release element (82) when the actuating element (84) is repeatedly actuated, wherein the relative position of the release element (82) to the swivelling element (92) alternately changes between a first position for acting upon one swivelling arm (96) and a second position for acting upon the other swivelling arm (98) when the actuating element (84) is repeatedly actuated.

18. The device as defined in claim 1 wherein a gas discharge valve (116) for discharging gas synchronously with the medium discharge is provided, that said gas discharge valve (116) comprises a first and a second chamber (124,126) which are connected with each other, wherein said first chamber (124) has a larger cross-section that said second chamber (126), between the two chambers (124,126) a shoulder area is provided, the two chambers (124,126) comprise inlets (118,129) for the in-flow of pressurized gas from a common compressed-gas source, said first chamber (124) is additionally provided with a vent hole (130) which is adapted to be closed by a closing element (132) biased into the closed position, which closing element (132) is movable against the bias into an open position when the release element (82) is actuated, said second chamber (126) comprises a gas outlet (114), and in the two chambers (124,126) a displaceable control piston (122) is arranged which, in its position as bearing upon the shoulder area, closes the gas outlet (114) of said second chamber (126), and, when removed from the shoulder area, clears the gas outlet (114) of said second chamber (126).

19. The device as defined in claim 2 wherein a gas discharge valve (116) for discharging gas synchronously with the medium discharge is provided, that said gas discharge valve (116) comprises a first and a second chamber (124,126) which are connected with each other, wherein said first chamber (124) has a larger cross-section that said second chamber (126), between the two chambers (124,126) a shoulder area is provided, the two chambers (124,126) comprise inlets (118,129) for the in-flow of pressurized gas from a common compressed-gas source, said first chamber (124) is additionally provided with a vent hole (130) which is adapted to be closed by a closing element (132) biased into the closed position, which closing element (132) is movable against the bias into an open position when the release element (82) is actuated, said second chamber (126) comprises a gas outlet (114), and in the two chambers (124,126) a displaceable control piston (122) is arranged which, in its position as bearing upon the shoulder area, closes the gas outlet (114) of said second chamber (126), and, when removed from the shoulder area, clears the gas outlet (114) of said second chamber (126).

20. The device as defined in claim 3 wherein a gas discharge valve (116) for discharging gas synchronously with the medium discharge is provided, that said gas discharge valve (116) comprises a first and a second chamber (124,126) which are connected with each other, wherein said first chamber (124) has a larger cross-section that said second chamber (126), between the two chambers (124,126) a shoulder area is provided, the two chambers (124,126) comprise inlets (118,129) for the in-flow of pressurized gas from a common compressed-gas source, said first chamber (124) is additionally provided with a vent hole (130) which is adapted to be closed by a closing element (132) biased into the closed position, which closing element (132) is movable against the bias into an open position when the release element (82) is actuated, said second chamber (126) comprises a gas outlet (114), and in the two chambers (124,126) a displaceable control piston (122) is arranged which, in its position as bearing upon the shoulder area, closes the gas outlet (114) of said second chamber (126), and, when removed from the shoulder area, clears the gas outlet (114) of said second chamber (126).

21. The device as defined in claim 5 wherein a gas discharge valve (116) for discharging gas synchronously with the medium discharge is provided, that said gas discharge valve (116) comprises a first and a second chamber (124,126) which are connected with each other, wherein said first chamber (124) has a larger cross-section that said second chamber (126), between the two chambers (124,126) a shoulder area is provided, the two chambers (124,126) comprise inlets (118,129) for the in-flow of pressurized gas from a common compressed-gas source, said first chamber (124) is additionally provided with a vent hole (130) which is adapted to be closed by a closing element (132) biased into the closed position, which closing element (132) is movable against the bias into an open position when the release element (82) is actuated, said second chamber (126) comprises a gas outlet (114), and in the two chambers (124,126) a displaceable control piston (122) is arranged which, in its position as bearing upon the shoulder area, closes the gas outlet (114) of said second chamber (126), and, when removed from the shoulder area, clears the gas outlet (114) of said second chamber (126).

22. The device as defined in claim 8 wherein a gas discharge valve (116) for discharging gas synchronously with the medium discharge is provided, that said gas discharge valve (116) comprises a first and a second chamber (124,126) which are connected with each other, wherein said first chamber (124) has a larger cross-section that said second chamber (126), between the two chambers (124,126) a shoulder area is provided, the two chambers (124,126) comprise inlets (118,129) for the in-flow of pressurized gas from a common compressed-gas source, said first chamber (124) is additionally provided with a vent hole (130) which is adapted to be closed by a closing element (132) biased into the closed position, which closing element (132) is movable against the bias into an open fat position when the release element (82) is actuated, said second chamber (126) comprises a gas outlet (114), and in the two chambers (124,126) a displaceable control piston (122) is arranged which, in its position as bearing upon the shoulder area, closes the gas outlet (114) of said second chamber (126), and, when removed from the shoulder area, clears the gas outlet (114) of said second chamber (126).

23. The device as defined in claim 9 wherein a gas discharge valve (116) for discharging gas synchronously with the medium discharge is provided, that said gas discharge valve (116) comprises a first and a second chamber (124,126) which are connected with each other, wherein said first chamber (124) has a larger cross-section that said second chamber (126), between the two chambers (124,126) a shoulder area is provided, the two chambers (124,126) comprise inlets (118,129) for the in-flow of pressurized gas from a common compressed-gas source, said first chamber (124) is additionally provided with a vent hole (130) which is adapted to be closed by a closing element (132) biased into the closed position, which closing element (132) is movable against the bias into an open position when the release element (82) is actuated, said second chamber (126) comprises a gas outlet (114), and in the two chambers (124,126) a displaceable control piston (122) is arranged which, in its position as bearing upon the shoulder area, closes the gas outlet (114) of said second chamber (126), and, when removed from the shoulder area, clears the gas outlet (114) of said second chamber (126).

24. The device as defined in claim 14 wherein a gas discharge valve (116) for discharging gas synchronously with the medium discharge is provided, that said gas discharge valve (116) comprises a first and a second chamber (124,126) which are connected with each other, wherein said first chamber (124) has a larger cross-section that said second chamber (126), between the two chambers (124,126) a shoulder area is provided, the two chambers (124,126) comprise inlets (118,129) for the in-flow of pressurized gas from a common compressed-gas source, said first chamber (124) is additionally provided with a vent hole (130) which is adapted to be closed by a closing element (132) biased into the closed position, which closing element (132) is movable against the bias into an open position when the release element (82) is actuated, said second chamber (126) comprises a gas outlet (114), and in the two chambers (124,126) a displaceable control piston (122) is arranged which, in its position as bearing upon the shoulder area, closes the gas outlet (114) of said second chamber (126), and, when removed from the shoulder area, clears the gas outlet (114) of said second chamber (126).

25. The device as defined in claim 15 wherein a gas discharge valve (116) for discharging gas synchronously with the medium discharge is provided, that said gas discharge valve (116) comprises a first and a second chamber (124,126) which are connected with each other, wherein said first chamber (124) has a larger cross-section that said second chamber (126), between the two chambers (124,126) a shoulder area is provided, the two chambers (124,126) comprise inlets (118,129) for the in-flow of pressurized gas from a common compressed-gas source, said first chamber (124) is additionally provided with a vent hole (130) which is adapted to be closed by a closing element (132) biased into the closed position, which closing element (132) is movable against the bias into an open position when the release element (82) is actuated, said second chamber (126) comprises a gas outlet (114), and in the two chambers (124,126) a displaceable control piston (122) is arranged which, in its position as bearing upon the shoulder area, closes the gas outlet (114) of said second chamber (126), and, when removed from the shoulder area, clears the gas outlet (114) of said second chamber (126).

26. The device as defined in claim 17 wherein a gas discharge valve (116) for discharging gas synchronously with the medium discharge is provided, that said gas discharge valve (116) comprises a first and a second chamber (124,126) which are connected with each other, wherein said first chamber (124) has a larger cross-section that said second chamber (126), between the two chambers (124,126) a shoulder area is provided, the two chambers (124,126) comprise inlets (118,129) for the in-flow of pressurized gas from a common compressed-gas source, said first chamber (124) is additionally provided with a vent hole (130) which is adapted to be closed by a closing element (132) biased into the closed position, which closing element (132) is movable against the bias into an open position when the release element (82) is actuated, said second chamber (126) comprises a gas outlet (114), and in the two chambers (124,126) a displaceable control piston (122) is arranged which, in its position as bearing upon the shoulder area, closes the gas outlet (114) of said second chamber (126), and, when removed from the shoulder area, clears the gas outlet (114) of said second chamber (126).

27. The device as defined in claim 1 wherein upstream of the gas inlet (129) of the first chamber (124) a flow restrictor (138) is provided, or said gas inlet (129) is configured as a flow restrictor, wherein the gas entering said first chamber (124) flows through a passage area with a smaller cross-section than the gas entering the second chamber (126).

* * * * *